(12) United States Patent
Klaveness

(10) Patent No.: US 7,262,862 B2
(45) Date of Patent: Aug. 28, 2007

(54) MEASUREMENT OF A 3D SURFACE OF AN OBJECT DURING PRESSURE EXPOSURE

(75) Inventor: Bjørn Klaveness, Tjodalyng (NO)

(73) Assignee: Klaveness Skofabrikk AS, Sandefjord (NO)

( * ) Notice: Subject to any disclaimer, the term of this patent is extended or adjusted under 35 U.S.C. 154(b) by 0 days.

(21) Appl. No.: 10/548,785

(22) PCT Filed: Feb. 10, 2004

(86) PCT No.: PCT/NO2004/000039

§ 371 (c)(1),
(2), (4) Date: Jan. 4, 2006

(87) PCT Pub. No.: WO2004/071297

PCT Pub. Date: Aug. 26, 2004

(65) Prior Publication Data

US 2006/0103852 A1 May 18, 2006

(30) Foreign Application Priority Data

Feb. 11, 2003 (NO) .................................. 20030674

(51) Int. Cl.
*G01B 11/24* (2006.01)
*G06K 9/00* (2006.01)

(52) U.S. Cl. ...................................... 356/601; 382/154

(58) Field of Classification Search ................ 356/601, 356/603, 608, 611, 613
See application file for complete search history.

(56) References Cited

U.S. PATENT DOCUMENTS

| 5,336,459 | A | * | 8/1994 | Barna .......................... 264/223 |
| 5,800,364 | A | * | 9/1998 | Glennie et al. ............. 600/592 |
| 6,829,377 | B2 | * | 12/2004 | Milioto ....................... 382/128 |
| 7,068,379 | B2 | * | 6/2006 | Sundman et al. ........... 356/601 |

FOREIGN PATENT DOCUMENTS

DE      44 04 695 C2     8/1995

\* cited by examiner

Primary Examiner—Roy M. Punnoose
(74) Attorney, Agent, or Firm—Senniger Powers

(57) ABSTRACT

A method for measuring the 3D surface (15) of an object (14) in order to describe its form digitally. The object is pressed down on a membrane (6) so as to make an imprint to be transferred to a medium (4) below. Said medium can at the same time be exposed to a pressure for controlling the submerging therein. The imprint under the object (14) is scanned from below, through the medium (4), and particularly the transparency of the medium is registered in each scanning point to give a base for estimating the height up to the imprint and thereby the third dimension (z) of the surface (15). The pressure applied to a medium (4) can as an example be useful by the production of foot beds when said object (14) is a foot, together with a scanning result of an imprint where the imprint is made by an even pressure distribution at the downward-facing surface.

10 Claims, 2 Drawing Sheets

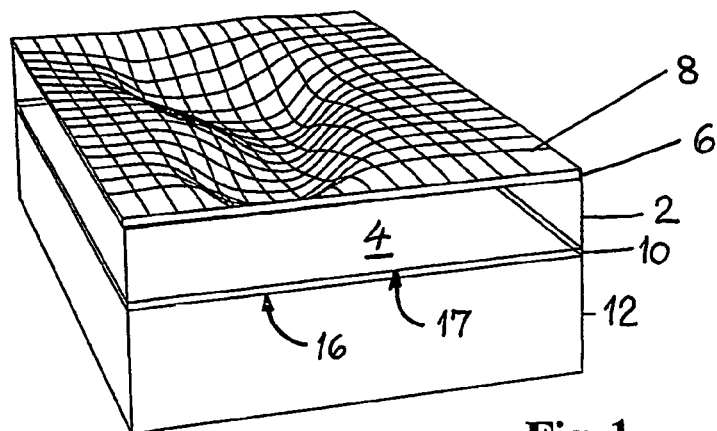
Fig. 1
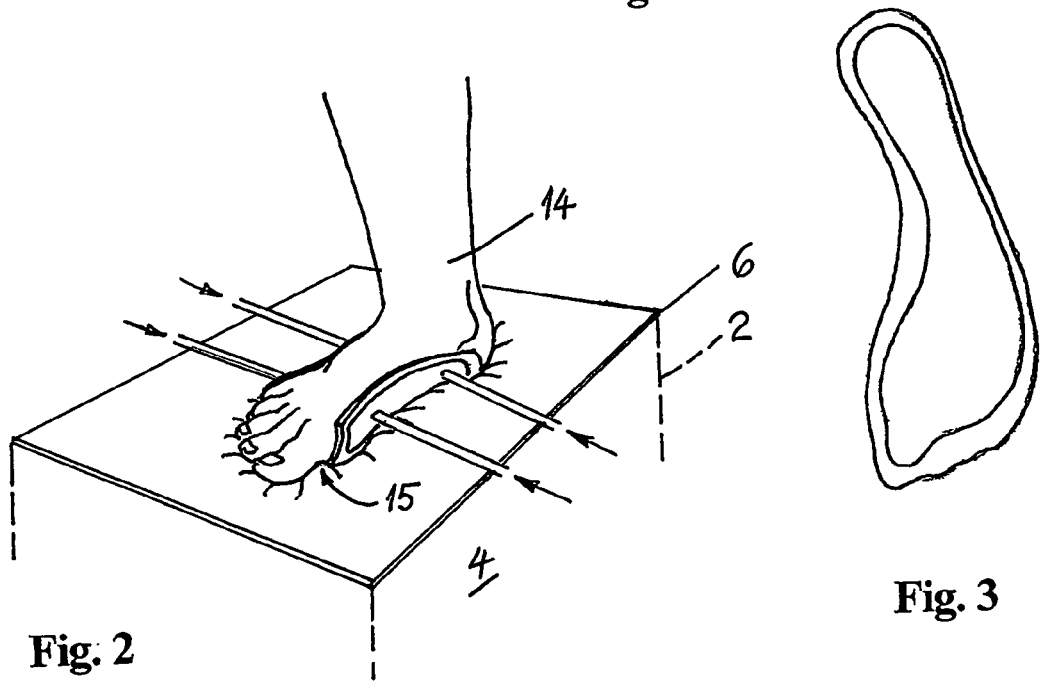
Fig. 2
Fig. 3
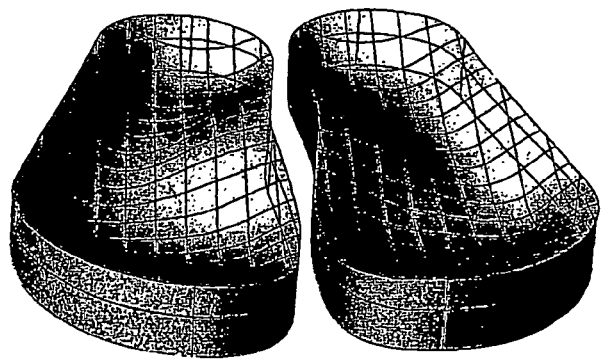
Fig. 4

MEASUREMENT OF A 3D SURFACE OF AN OBJECT DURING PRESSURE EXPOSURE

FIELD OF THE INVENTION

The present invention generally is directed to the measurement of the three dimensional (3D) form of surfaces. In particular the invention can be used to register/measure/map the outer form of a foot or another body part, comprising the surface of a leg or arm trunk so that a prosthesis can be made. Body parts comprise of soft tissue like skin, fat and muscles, and harder elements like tendons and bones, less deformable. By applying a pressure to the actual body part during the registering of the surface thereof, its form can be altered in a desired direction.

BACKGROUND OF THE INVENTION

Earlier foot beds were made by using a foot mould or impression in a foam material. Pressing the foot on to a glass plate is also an easy way to study the foot print from below. Today scanning equipment (scanners) can also be used for 3D mapping of an object or a surface, but such equipment tends to be fairly expensive and additionally suffers by needing a surface pressure against the object, for example from below by the glass plate under the foot. The important possibility to load an object like a foot by applying a hydrostatic or gas pressure during a scanning sequence, does not seem to have been suggested until now.

BRIEF SUMMARY OF THE INVENTION

A purpose for the present invention therefore generally is to provide a method for measuring the 3D surface of an object, also when said object is exposed for a pressure loading. Another purpose is a device for carrying out said method. A solution is proposed by the method cited in appended patent claim 1 and being characterised by the following features:

A submerging of the object in a deformable and optically semi-transparent medium that can be observed from the downward-facing surface thereof, so that also the surface of the downward-facing surface of the object can be observed through said medium, a point by point depicting of the projection of said object through said medium at the downward-facing surface thereof, in an image plane of which each image point (x, y, $z_0$) is referred to two orthogonal, particularly horizontal directions x and y but having the same vertical heights ($z_0$) over a reference plane ($z \approx 0$), a registering of the intensity and/or colour of the light being emitted from each point (x, y, z) at the surface, passing the medium and falling on corresponding image points (x, y, $z_0$) in said image plane, a coordination between the result from the registering of the intensity and/or colour of said points and data for the medium and the image, an estimation of the height ($z-z_0$) from said image plane up to each point (x, y, z) of the surface and/or the estimation of the surface inclination in each of same points in relation to said image plane, based upon the result of the co-ordination and in order to determine the 3D form of the surface of the object at the downward-facing surface thereof, and a further processing for presentation and storing the obtained results.

The submerging of the object into the medium is effectuated through a membrane covering its surface and having a coloured or white downward-facing surface making it easy to observe or scan from below, even through the medium, if this is in the form of a transparent fluid like water or gas. A scanning or depicting from below can also be facilitated if the membrane downward-facing surface has a rectangular grid, means for fluorescence or phosphorescence, point patterns, reflection elements or the like, so that enough light for a scanning is reflected back to give a good resolution in an image plane.

If the medium is a compressible fluid like a resilient semi-transparent gel or a gas, it can itself have a colour that changes with the grade of compression. A control of the external and/or the internal pressure of the medium will make an object sink more or less down into it. Further, if the object is a foot or generally can be deformed to a certain degree, the pressure control will also have the effect that the outer form will change somewhat, dependent of the pressure.

Finally the invention consists of a device to carry out said method, said device in particular comprising a vessel filled with a deformable medium and having a transparent bottom of which the downward-facing surface is plane and horizontal, means for scanning and imaging of the downward-facing surface of the vessel, means for processing the result from the scanning, and a membrane covering the upward-facing surface or upper side of the medium.

The medium is an optically semi-transparent fluid in the form of a liquid, a gel or a gas, and the means for scanning/imaging and the means for processing are, in particular, provided for recording the intensity and/or the colour of the light from each point (x, y, z) at the surface of the downward-facing surface of the object, said light passing the medium and falling on to the corresponding point (x, y, $z_0$) in the image plane, co-ordination between the result from the recording of the intensity and/or colour of said points and data for said medium and said image, estimating the height ($z-z_0$) from the image plane up to each point (x, y, z) at the surface and/or estimating the inclination of said surface in each of the same points relative to the image plane, based upon the result of the co-ordination and such that the 3D form of the surface on the downward-facing surface or upper side of the object is determined, and presentation and storing the obtained results.

Especially when the medium is a coloured and semi-transparent liquid, its optical transparency will normally be proportional with the liquid level over each point in the image plane (see the comment below regarding the thickness of the vessel bottom) and may serve as a parameter for determining this height ($z-z_0$) and thereby for example the 3D outline of a depressed foot.

The means used for further processing comprise one or several units from the following group: a first pressure transducer for the medium or its environment, a computer, a program for the scanner, a data base, a memory, a display, a second pressure transducer for additional pressure against the object, a communication bus, a processing unit.

A preferred object is a body part, in particular a foot.

It should be noted that the image of the downward-facing surface of the object will become an indirect image when a membrane is used between the downward-facing surface and the medium, so that for example the outline of the foot finally has to be found by removing the membrane thickness. A corresponding inaccuracy is also due to the thickness of the vessel bottom, in that the image plane for practical reasons is at the downward-facing surface of the transparent bottom.

Due to the present invention the limitations known from the previous prior art are avoided by using a surrounding medium as for a mould imaging process, combined with a foot imprint measurement resembling that of the foot on a glass plate. According to the invention the pressure of the object to the medium and the medium pressure itself can be varied. The same principals were also used for providing an additional pressure over certain areas of for example a foot, in order to analyse its corresponding form variations. A mapping of the result in a machine readable format uses modern two dimensional (2D) scanning and is according to the invention expanded to a full 3D presentation. The results are in digital format at the presentation, so that they can easily be processed and coordinated in various applications.

BRIEF DESCRIPTION OF THE DRAWINGS

The invention is described in detail below, namely some typical and preferred embodiments. The drawings are also referred to, for typical situations and examples, wherein:

FIG. 1 shows an imprint of an object pressed down into a deformable medium to be scanned/analysed from below, FIG. 2 shows a setup as in FIG. 1 having a foot as the object and an additional side pressure being applied thereto, FIG. 3 is a view from below of foot imprints obtained by varying the medium pressure and giving an inner outline for a fairly high pressure and an outer one for a lower pressure, FIG. 4 illustrates two foot bed surfaces generated according to the invention.

DETAILED DESCRIPTION OF THE INVENTION

Figure 5:
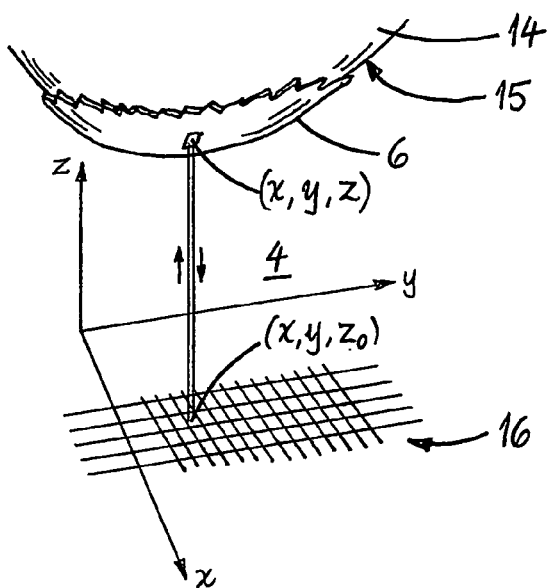
FIG. 5 illustrates a scanning principle from an image plane and the registering of reflected light in the same plane from a point of an object.

FIGS. 1 and 2 illustrate a typical setup for the measurement of the downward-facing surface surface 15 of an object 14 (see FIG. 2) in 3D representation. The surface 15 form is measured indirectly as an imprint or footprint, and the object is preferably a human foot. A rectangular vessel 2 is filled with a medium 4 that can be a semi-transparent liquid, and a membrane 6 of for example rubber covering said vessel top. The membrane 6 has preferably a square grid 8 made of crossing lines so that the imprint is clearly visible, which is the usual way for an outline presentation supported by most 3D programmes. Said membrane 6 is preferably also white to make it visible from below, through the bottom 10 of the vessel 2 and the medium 4. As mentioned above, the medium is semi-transparent, and the bottom 10 is of transparent plexiglass or similar. The vessel 2 is mounted directly above a scanner 12 using an image plane 16 (see also FIGS. 5 and 6) for scanning the downward-facing surface 17 of the medium 4 and provides an image of the downward-facing surface of the membrane 6 through said medium 4. In practice the scanning is performed from the downward-facing surface of the glass bottom 10, which is less thick compared to the height of the medium. An impression of a submerged object 14 therefore will look lighter or darker in an image in the scanner 12, depending on how far the object is pressed down into the medium. This light indication is registered for each picture element and is used for the estimation of the height up to each imprint point. The scanner 12 can be in the so called flat bed version. An important feature of the invention is in the constitution of the medium 4. In a preferred form the medium is a liquid having optical semi-transparency and fairly dark colour. By the co-ordination of the result from the registering of the transparency of the liquid, with the x y co-ordinates for the object and corresponding to the co-ordinates of the image plane 16, a 3D image is obtained of the object outline, including the membrane 6.

The counteracting pressure of the liquid as the medium 4 against the submerged object on the membrane 6 can be adjusted by varying the environment pressure of the vessel 2, for example by connecting said vessel with a liquid supply container that can be raised and lowered so that a liquid displacement in the vessel 2 will meet a varying force. In this way an optimal action on a resilient object can be obtained, as on the soft parts of a foot (muscles, fat, tendons etc.) and hard bones, in order to obtain the best possible pressure and force distribution. The aim can be the production of soles, shoes and foot beds. By using the vessel pressure as a parameter an additional means is obtained for analysing the properties of a resilient object 14, to a greater degree than what apparently has been demonstrated until now.

In a further development and illustrated in FIG. 2 for the outline measurement of a foot, an additional pressure is applied against its sides, mainly for simulating the action from a narrow shoe. Corresponding simulations for other body parts have also proved useful for prosthesis adaptation purposes.

It should be noted that the example in FIG. 1 uses a semi-transparent liquid, but the invention is of course not limited to this example and all types of media can be suitable for special applications, comprising gels, gases, multiphase fluids and the like. Compared to a pure liquid such media can also be compressible, and it is fully possible to exploit the varying compression of such media at the downward-facing surface of a submerged object in a corresponding way. As an example the vessel 2 can contain a compressible medium of which the colour varies depending on the pressure on the different places.

A pressure control of such a medium can also be actual, and as with a liquid the pressure can easily be adjusted by raising/lowering an external container being connected to the fluid volume in said vessel 2, or the pressure can be controlled in other ways, comprising the use of a pump or another form of a pressure source or transducer.

FIG. 3 of the drawings illustrates two typical images of a foot 14 resting on the membrane 6, the medium 4 below and the glass bottom 10 of the vessel 2. The inner outline shows the situation when the medium pressure is fairly high, while the outer outline shows the same for a lower pressure.

FIG. 4 shows in a perspective and from the front two foot beds the surface of which being generated from the 3D surface or outline obtained by means of the method according to the invention.

FIG. 5 shows in further detail how an image is generated in the image plane 16 at the downward-facing surface of the glass bottom 10 during the scanning from below when a rubber membrane 6 having a light coloured downward-facing surface is pressed down into the medium 4. The image is generated from the light being transmitted from each point at the downward-facing surface of the membrane, or simplified: at the surface 15 of the object underside. The scanning is performed by emitting light perpendicularly up from each point $(x, y, z_0)$ in the image plane 16, thereafter to be reflected mainly in the same direction from each corresponding point $(x, y, z)$ on the membrane below the surface 15. The greater the distance between the object surface and the bottom 10 or the image plane 16, the higher the column of dark liquid has to be passed and the darker the image of the point will be, viewed from the downward-facing surface of the vessel 2.

The object 14 illustrated in FIG. 5 can be a heel and is shown on a segment of a membrane 6. A scanning beam from a point near the right edge of the drawing will in this case hit the membrane—following the surface 15—in a point at an angle to the horizontal image plane 16, so that the reflected light from this point goes into a different main direction than the vertical. Therefore only scattered light will fall on the scanner detector in the light emission point, resulting in the detector registering less light from the reflection point, which is the equivalent of a perpendicular reflection from a point higher up and thereby more attenuated due to the longer distance through the medium. The estimated height $z-z_0$ therefore will be greater than the real value. However, this can be corrected by utilizing a suitable computer programme. In certain applications this circumstance can also be used as a benefit, inter alia if the medium 4 is crystal clear and the scanning is not focused, as the reflection from a point on a horizontal surface will then be the same independent of the height over the image plane, but instead dependent on the light scattering property of the downward-facing surface of the membrane. Other types of images for this property can be used differently.

As mentioned above, the scanner 12 is used for emitting light towards the object and collecting reflected light from it. Using a suitable standard computer programme, the received light signals from each point can be converted into a digital format. Each image point or picture element (pixel) thereby is connected to a given colour or grey tone. Thereafter the image can be opened in a 3D computer programme for generating a 3D surface having one dimension (in this example the z direction) varying as a function of the colour saturation or the grey tone in each picture element.

Figure 6:
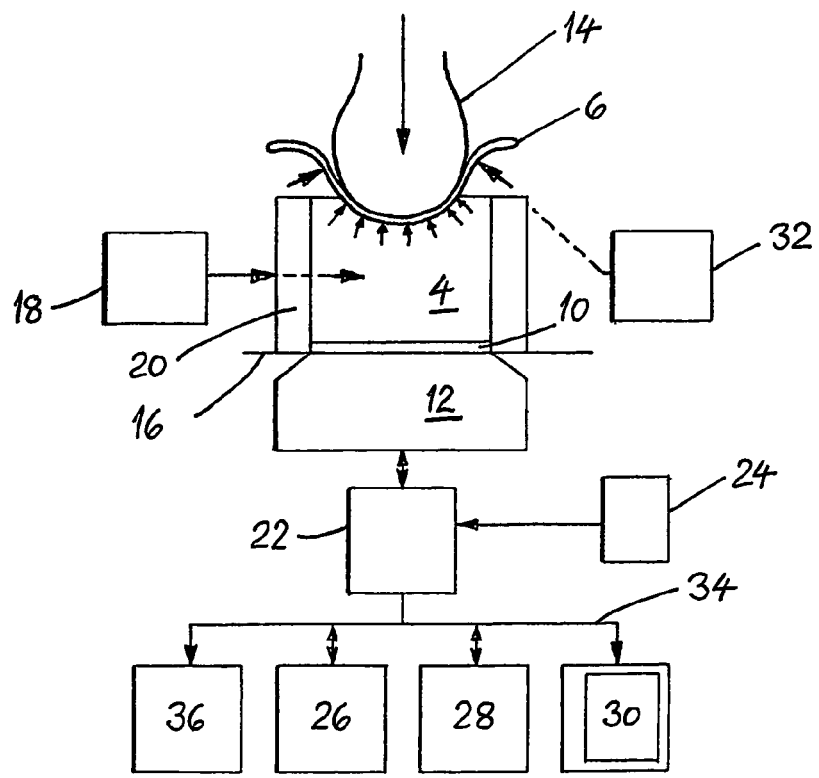
FIG. 6 is a block diagram over a typical apparatus for the purpose of foot surface measuring, analysing and presentation according to the invention.

FIG. 6 illustrates schematically a block diagram over a typical setup or arrangement for using the method according to the invention. The object 14 is a foot that presses the membrane 6 downward into the medium 4 in the vessel 2, and this is now shown within an outer environment 20 illustrating the application of forces or pressure, in this case using a first pressure transducer 18. A second transducer 32 corresponds to the illustration of FIG. 2, where the foot is also exposed to pressure from the sides, either from above or below through the membrane 6. The image plane 16 is seen below the vessel bottom 10, on the top of the scanner 12. A block indicates a computer programme 24. The scanning results are fed from the scanner 12 output to a computer 22 or processor on the output of which a communication bus 34 is connected to peripheral units, here shown as a data base 26, a memory 28, a display (a computer screen) 30 and a processing machine equipment 36.

The membrane form and thereby also the form of the submerged object can in this way be expressed mathematically (digitally) and can be processed in a computer. Instead of a scanner 12 of conventional type, other observation units such as cameras and similar can be used.

The results of the measurements and the subsequent processing in the machine equipment 36 or similar can be used for the manufacturing of prostheses, foot beds and similar, particularly under numerical (digital) command. The machine equipment 36 can comprise machinery such as mills, equipment for "rapid prototyping" etc.

By using conventional image processing it is fully possible to adjust, focus and vary the images of the 3D registered surface, and as an example an increase in black of 1% in a black and white image can correspond to a rising of 1 mm of the object.

An Example of a Method for the Manufacture of a Foot Bed.

1. The foot 14 of a person is placed upon the membrane 6 on the top of the medium 4.
2. The pressure of the medium or its environment is regulated to a desired level, depending on the weight of the person.
3. A plane image of the foot imprint is projected to the image plane 16 at the downward-facing surface and is visible from below, by the scanner 12. The colours or grey tones of the image provide additional information regarding the distance from each point at the surface 15 of the foot, to the vessel glass bottom 10.
4. The image is registered by the scanner and stored in the computer 22, together with the additional information for each depicted element.
5. The complete image information is processed in the computer 22 and stored and presented in a digital format by means of a 3D computer programme 24. The presentation represents the 3D surface 15 of the foot 14 when said foot is exposed for a desired counteracting pressure from the medium 4 via the membrane 6.
6. The thereby stored data for the foot surface 15 can be compared to previously generated and stored data (26, 28) for the surface of the same foot in order to see developments and changes in the foot shape.
7. The recently stored data for the foot surface 15 is processed, delimited in the programme and moved to a data file (26, 28) for the use of remedies, aids and facilities etc.
8. The file is transferred to machine equipment (36), for example a CNC mill for the production of a foot bed or similar.

The invention claimed is:

1. A method for measuring the 3D surface of an object, characterized in:

a submerging of the object in a deformable and optically semi-transparent medium that is observable from a downward-facing surface thereof, so that a surface of the downward-facing surface of the object is also observable through said medium, a point by point depiction of the projection of said object through said medium at the downward-facing surface thereof, in an image plane of which each image point is referred to two orthogonal, particularly horizontal directions x and y but having the same vertical heights over a reference plane, a recording of the intensity and/or colour of the light being emitted from each point at the surface, passing the medium and falling on corresponding image points in said image plane, a co-ordination between results from the recording of the intensity and/or colour of said points and data for the medium and the image, an estimation of the height from said image plane up to each point of the surface and/or the estimation of the surface inclination in each of same points in relation to said image plane, based upon the result of the co-ordination and in order to determine the 3D form of the downward-facing surface of the object, and a processing for presentation and storing the obtained results.

2. The method according to claim 1, characterised in that the submerging of the object into the semi-transparent medium is carried out through a membrane covering the upper surface of said medium, the membrane downward-facing surface being suitable for a point by point depiction from the underside of the medium.

3. The method according to claim 2, characterised in that the downward-facing surface of the membrane, in order to be suitable for the depiction from below comprises one or several of the following means: contrast colours, a rectangular grid, means for fluorescence, means for phosphorescence, point patterns or reflection elements, so that sufficient light for the depiction and imaging falls on the points in the image plane.

4. The method according to claim 1, characterised in that the optically semi-transparent medium is a liquid or a compressible fluid, particularly a deformable gel or a gas, comprising pure air.

5. The method according to claim 1, characterised in that the medium is compressible and having a colour changing with the grade of compression.

6. The method according to claim 1, characterised in that the environment pressure around and/or the internal pressure of the medium is controlled to provide a varying submerging of an object which at least partly is deformable, so that the surface of said object will change its form depending upon the pressure.

7. The method according to claim 1, characterised in applying an additional pressure against the object, in addition to the controllable own pressure of the medium, in order to simulate given pressure conditions for deformable objects.

8. The method according to claim 1, characterised in that the object is a body part, particularly a foot.

9. A device for carrying out the method according to claim 1, comprising:

a vessel filled with a deformable medium and having a transparent bottom of which the downward-facing surface is plane and horizontal, means for scanning and imaging the downward-facing surface of the vessel, and means for the processing of the result from the scanning, the device being characterised by:

a membrane covering the upward-facing surface of the medium, said medium being an optically semi-transparent fluid in the form of a liquid, a gel or a gas, and said means for scanning/imaging and said means for processing being provided for the:

recording of the intensity and/or the colour of the light from each point at the surface of the underside of the object, said light passing the medium and s falling on the corresponding image point in the image plane, co-ordination between the result from the recording of the intensity and/or colour of said points and data for said medium and said image, estimation of the height from the image plane up to each point at the surface and/or estimating the inclination of said surface in each of the same points relative to the image plane, based upon the result of the co-ordination and such that the 3D form of the surface on the downward-facing surface of the object is determined, and presentation and storing the obtained results.

10. Device according to claim 9, characterised in that said means for the processing comprise one or several units from the following group: a first pressure transducer for the medium or its environment, a computer, a programme for the scanner, a data base, a memory, a display, a second pressure transducer for additional pressure against the object, a communication bus, a processing unit.

* * * * *